United States Patent [19]
Kaltenbach

[11] Patent Number: 5,131,406
[45] Date of Patent: Jul. 21, 1992

[54] GUIDE FOR INTRODUCTION OF CATHETERS INTO BLOOD VESSELS AND THE LIKE

[76] Inventor: Martin Kaltenbach, Falltorweg 8, D-6072 Dreieich-Buchschlag, Fed. Rep. of Germany

[21] Appl. No.: 585,293

[22] Filed: Sep. 19, 1990

[30] Foreign Application Priority Data

Sep. 20, 1989 [DE] Fed. Rep. of Germany ........ 3931350

[51] Int. Cl.$^5$ ................................................ A61B 5/00
[52] U.S. Cl. ................................ 128/772; 128/657; 604/95
[58] Field of Search ................ 128/657, 772; 604/95, 604/264, 280

[56] References Cited

U.S. PATENT DOCUMENTS

| | | | |
|---|---|---|---|
| 3,547,103 | 12/1970 | Cook | 604/95 |
| 3,749,085 | 7/1973 | Willson | 128/2 B |
| 3,749,086 | 7/1973 | Kline et al. | 604/95 |
| 4,020,829 | 5/1977 | Willson | 128/2 M |
| 4,215,703 | 8/1980 | Willson | 604/95 |
| 4,724,846 | 2/1988 | Evans | 128/657 |
| 4,798,598 | 1/1989 | Bonello et al. | 604/95 |
| 4,800,890 | 1/1989 | Cramer | 604/95 |
| 4,846,186 | 7/1989 | Box et al. | 604/280 |
| 4,917,102 | 4/1990 | Miller et al. | 128/657 |

FOREIGN PATENT DOCUMENTS

| | | | |
|---|---|---|---|
| 3532563 | 3/1986 | Fed. Rep. of Germany . | |
| 0012069 | 1/1985 | Japan | 128/772 |

*Primary Examiner*—Max Hindenburg
*Attorney, Agent, or Firm*—Peter K. Kontler

[57] ABSTRACT

A guide which can be introduced into a narrow passage in a human or other animal body, such as into a narrow blood vessel in a human heart, has a flexible tube which is made of a plurality of helically wound and closely adjacent wires of a metallic or plastic material. An intermediate portion of the tube adjacent its distal end is permanently curved or is ductile so that its curvature can be changed in order to enable a person in charge to select the orientation of the distal end of the tube for convenient advancement from a wider passage into a narrower passage which is inclined with reference to the wider passage. The inserted tube serves as a guide for introduction of a dilatation catheter, another catheter, a cardiac pacemaker electrode or any other slender elongated flexible medical device which is to be temporarily or permanently introduced into the heart or into another organ or another part of an animal body. The making of the tube from several helically wound wires ensures that the distal end is compelled to share angular movements of the proximal end while the flexibility of the tube remains very pronounced.

18 Claims, 2 Drawing Sheets

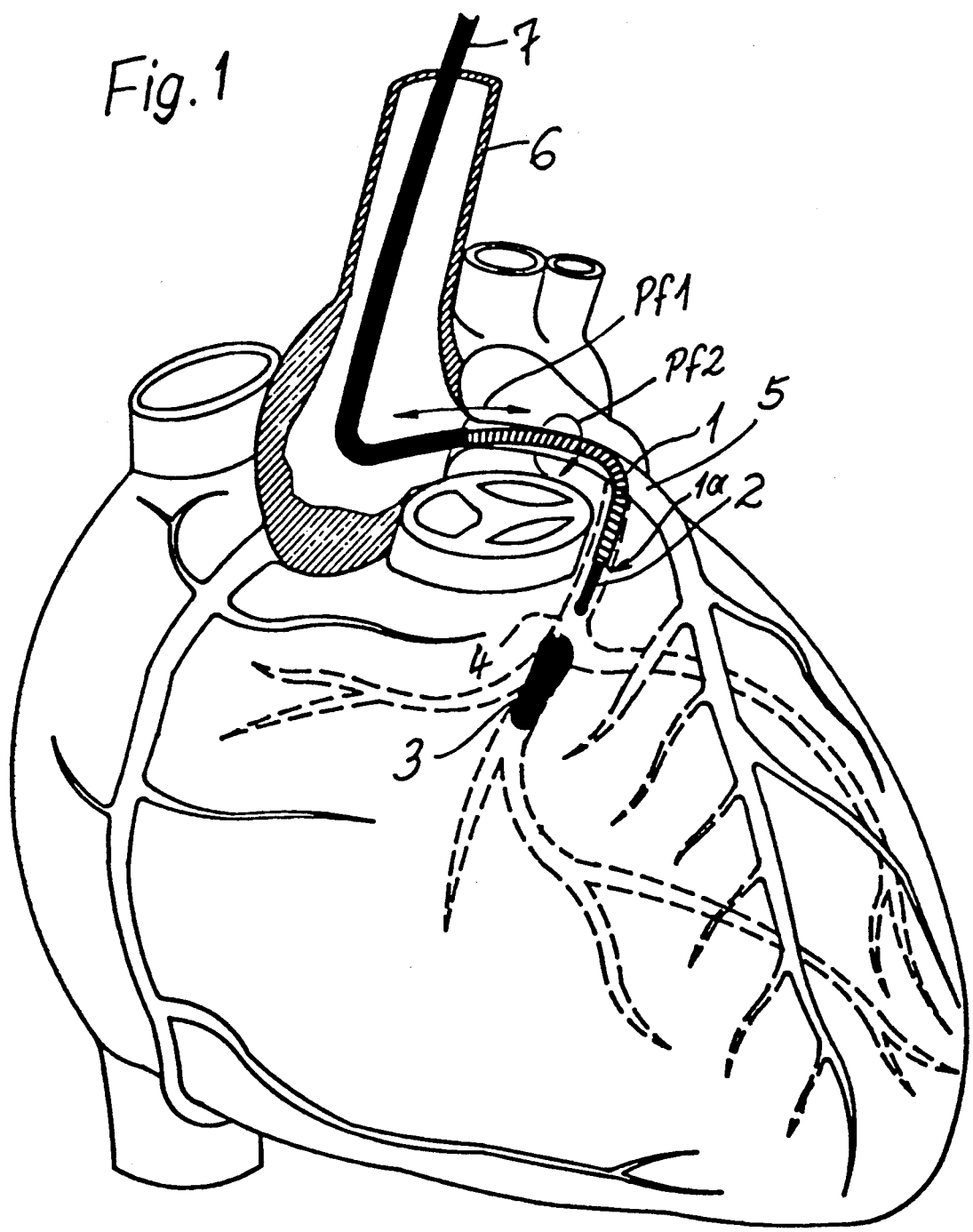

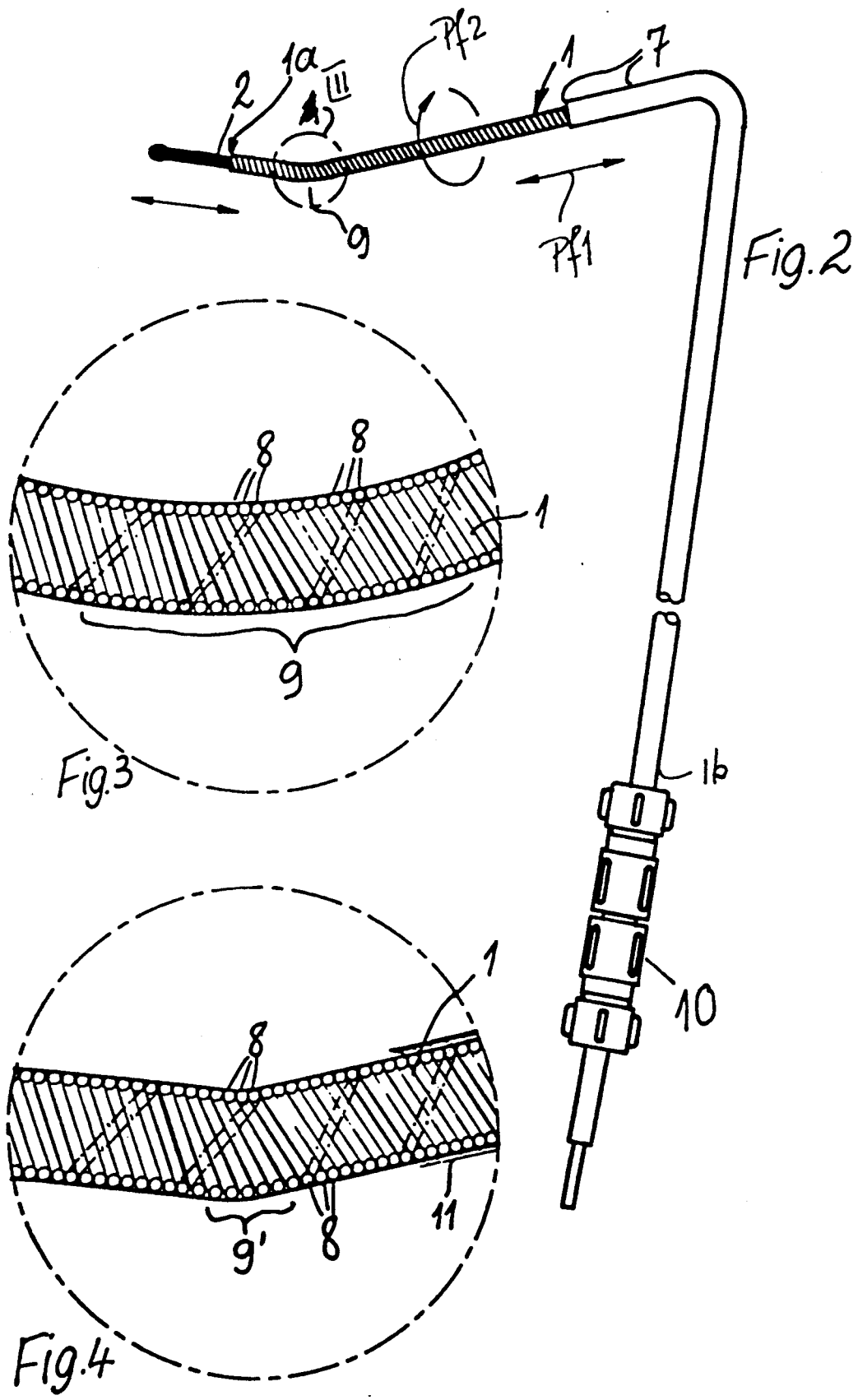

GUIDE FOR INTRODUCTION OF CATHETERS INTO BLOOD VESSELS AND THE LIKE

BACKGROUND OF THE INVENTION

The invention relates to improvements in implements for facilitating introduction of slender elongated flexible medical devices (such as rotary or other catheters or cardiac pacemaker electrodes) into cavities of animal bodies. More particularly, the invention relates to improvements in implements or instruments which can be utilized to advance elongated flexible medical devices along a complex path, especially from one or more wider passages into one or more narrower passages in a human heart or in another organ or part of an animal body.

When the working end of a rotary or other catheter must be introduced into a selected portion of an animal body by way of one or more blood vessels and/or other passages, it is often necessary to change the direction of advancement of the distal end of the catheter, for example, at the junction of a wider blood vessel with a narrower blood vessel which latter is inclined relative to the adjacent portion of the wider vessel. Heretofore known implements which are used to facilitate introduction of catheters include elongated flexible sleeves which are made of a plastic material. The sleeves can be used for introduction of the leading or distal end of a rotary dilatation catheter into a human heart. To this end, a plastic sleeve is introduced into a relatively large blood vessel which leads to the heart and communicates with one or more narrower vessels (branch passages). The distal end of the sleeve is positioned at the junction of the wider vessel with the narrower vessel, and the catheter is thereupon advanced in the inserted sleeve so that its distal or working end emerges from the distal end of the sleeve at the junction. The main purpose of the sleeve is to ensure that the working end of the catheter cannot contact and possibly injure the tissue around the wider passage while the working end of the catheter advances toward the junction. A rotary dilatation catheter is described and shown, for example, in published German patent application No. 35 32 653.

The aforediscussed conventional sleeve is of no help in introducing the distal end of the catheter from the wider into the narrower passage in an animal body, e.g., in a human heart. Thus, the sleeve does not and cannot assist the distal end of the catheter in finding its way from a wider passage into a narrower passage which is inclined relative to (e.g., which makes an acute angle with) the wider passage and must be entered by the distal end of the catheter. This problem of causing the distal end of a flexible catheter to make a sharp curve (e.g., a U-curve) on its way toward an obstruction in a relatively narrow passage in a human heart or in another organ or part of an animal body remained unsolved for many decades.

Attempts to steer the distal end of a catheter along an elongated path which has two or more mutually inclined portions include the utilization of pull strings (e.g., thin filaments) which are manipulated to change the orientation of the distal end at the junction of two mutually inclined passages. The pull strings are effective to direct the distal end of a flexible catheter toward the junction of two mutually inclined blood vessels or other passages in an animal body. However, the pull strings also exhibit a number of drawbacks, particularly as concerns the space requirements of the sleeve which confines the catheter and the strings. Thus, the wall thickness of the sleeve must suffice to provide channels for the pull strings. A relatively thick-walled sleeve cannot be readily flexed which creates problems in connection with introduction of the sleeve even into a larger blood vessel or another passage in an animal body. Moreover, a relatively stiff sleeve cannot permit a pronounced change of orientation of its distal end for the purpose of steering the distal end of a catheter into the inlet of a narrower passage which is inclined (e.g., at a relatively small acute angle) relative to a wider passage. It has been found that a sleeve which is capable of accommodating one or more pull strings to change the orientation of its distal end cannot be used for introduction of catheters into relatively narrow passages in a human heart or another organ. If the outer diameter of such sleeve is sufficiently small to permit insertion into a relatively narrow passage in a human heart, the inner diameter of the sleeve is much too small to permit introduction of a rotary or other dilatation catheter. A tubular guide with pull strings is disclosed in German Pat. No. 38 19 372 to Zeiher.

U.S. Pat. No. 3,749,085 to Willson et al. discloses a vascular tissue removing device which is formed by a multi-strand coil of wires. The ends of the wires are cut to define axially projecting radially offset cutters. Remote control means is provided to guide the tissue removing device.

U.S. Pat. No. 4,020,829 to Willson et al. discloses an instrument which employs a guide wire having a short flexible distal section connected with a relatively long multi-wire axial and rotary torque transmitting section. The purpose of the guide wire is to steer a soft, thin-walled flexible tubular catheter through the compound curves involved in the junctions between various arterial branches. The inserted tubular catheter is used for introduction of a fluid into a remote internal body passageway. The single-wire distal section of the guide wire is soldered to the multiple-wire proximal section. This guide wire can be said to constitute a flexible core for guidance of a tubular implement which surrounds the core during introduction into an arterial branch.

OBJECTS OF THE INVENTION

An object of the invention is to provide a novel and improved guide which can permit controlled introduction of a rotary or other catheter, a cardiac pacemaker electrode or another elongated slender flexible medical device into narrow passages of animal bodies even though it need not contain pull strings or any other discrete parts which are to be manipulated in order to change the orientation of the inserted distal end of the guide.

Another object of the invention is to provide a highly flexible guide which is constructed and assembled in such a way that it can change the orientation of its distal end in a simpler and more efficient manner than heretofore known guides.

A further object of the invention is to provide a thin-walled guide which can readily steer a rotary dilatation catheter or any other catheter into a desired part of a human heart or another organ or part of an animal body.

An additional object of the invention is to provide a guide which can be used for controlled insertion of available elongated flexible medical devices.

Still another object of the invention is to provide a novel and improved method of causing the distal end of a catheter or another elongated slender flexible medical device to advance along a path wherein neighboring path portions make an oblique angle, a right angle or an acute angle.

A further object of the invention is to provide a guide which permits rapid and convenient introduction of flexible medical devices without causing injury to the tissue around the passages leading to a selected location in an animal body.

Another object of the invention is to provide a guide which can be used with particular advantage for introduction of a rotary dilatation catheter into a relatively narrow passage in a human heart.

An additional object of the invention is to provide a simple and relatively inexpensive one-piece guide which can be used to accomplish the above outlined objects.

A further object of the invention is to provide a guide which is constructed and assembled in such a way that its distal end automatically assumes a desired orientation.

Another object of the invention is to provide a guide which can be rapidly adjusted or altered in a simple and time-saving manner in order to ensure injury-free introduction of the distal end of a catheter or another elongated flexible medical device into a selected part of an animal body.

SUMMARY OF THE INVENTION

The invention resides in the provision of a guide for introduction of rotary dilatation or other catheters, cardiac pacemaker electrodes and analogous slender elongated flexible medical devices into branch passages of human or other animal bodies, namely into passages which can be entered only by changing (once or more than once) the direction of advancement of the medical devices. The improved guide comprises a plurality of closely adjacent helically wound wires which together form a single elongated flexible rotary tube having a distal end, a proximal end and an intermediate portion which is adjacent the distal end and has a tendency to assume a curved shape so as to change the orientation of the distal end (and thus enable the distal end to enter a narrower passageway which branches off a wider passageway) in response to rotation of the tube.

The wires can include metallic and/or plastic wires, and the neighboring convolutions of the wires can be in actual contact with each other.

For example, the wires can consist of spring steel and can include soft annealed sections which together form the intermediate portion of the tube. These sections of the wires can be rendered ductile (so that they can be repeatedly flexed in the region of the intermediate portion) in any other suitable way. All that counts is to ensure that the distal end can be oriented by the intermediate portion to face the inlet of a narrower passage at the junction of such narrower passage with a wider passage.

The proximal end of the tube can be provided with means (e.g., a handle) for rotating the tube in order to change the orientation of the distal end.

The tube can consist of between two or three and nine or ten wires, for example, of between five and ten and preferably seven and eight wires. If at least some of the wires are made of steel, such material is preferably a corrosion-proof (stainless) steel. The diameter of each wire can be in the range of between 0.1 and 0.3 mm.

It is often preferred to make the tube in such a way that it comprises a first section adjacent the proximal end and a second section adjacent the distal end and including the intermediate portion. The first section consists of m (e.g., six to ten) helically wound wires, and the second section consists of m-n (e.g., two to five) helically wound wires. This ensures that the flexibility of the second section including the intermediate portion departs from the flexibility of the first section.

The guide can further comprise a flexible tubular envelope which surrounds at least a certain part of the tube. Such envelope can consist of or can contain a suitable plastic material and can be shrunk onto the tube. The envelope can be formed by spray coating, by extruding or in any other suitable way. The distal end (and preferably also the intermediate portion) of the tube extends or can extend beyond the envelope.

The novel features which are considered as characteristic of the invention are set forth in particular in the appended claims. The improved guide itself, however, both as to its construction and the mode of making and utilizing the same, together with additional features and advantages thereof, will be best understood upon perusal of the following detailed description of certain presently preferred specific embodiments with reference to the accompanying drawing.

BRIEF DESCRIPTION OF THE DRAWING

FIG. 1 is a schematic view of a human heart with the improved guide in the process of steering a dilatation catheter toward a blocked portion of a branch artery;

FIG. 2 is a fragmentary elevational view of the improved guide and of a sleeve which facilitates introduction of the tube of the improved guide into a large passageway;

FIG. 3 is an enlarged view of an intermediate portion of the improved guide within the phantom-line circle III in FIG. 2; and FIG. 4 is a similar view of a modified intermediate portion with a radius of curvature which is smaller than that of the intermediate portion of FIG. 3.

DESCRIPTION OF PREFERRED EMBODIMENTS

FIG. 1 shows a human heart which has a large passage or vessel 6 serving for introduction of a working catheter 2, such as a rotary dilatation catheter, which is to be introduced into a passage 4 branching off a larger branch passage 5 and containing an obstruction 3. The angle between the passages 4 and 5 is an acute angle and the distal end of the catheter 2 is capable of entering the passage 4 due to the provision of a novel guide the details of which are shown in FIGS. 2 and 3. The guide also serves to facilitate entry of the enlarged (thickened) distal end of the catheter 2 from the passage 6 into the passage 5 at an angle which approximates a right angle. The guide includes an elongated flexible rotary tube 1 having a distal end 1a and a proximal end 1b outside of the body containing the heart of FIG. 1. That part of the tube 1 which extends through the passage 6 and through the junction of passages 6 and 5 is surrounded by a flexible sleeve or hose 7 made of a suitable plastic material. The arrangement is such that the front end of the hose 7 is located at the locus where the tube 1 of the improved guide enters the branch passage 5.

In order to ensure that the tube 1 can properly advance from the branch passage 5 into the narrower branch passage 4 in spite of the very pronounced change in the direction of forward movement at the junction of these passages, the tube 1 is made of a plurality of closely adjacent parallel helically wound wires 8, for example, eight wires as actually shown in FIG. 3 wherein the front halves of convolutions of one of the eight wires 8 are indicated by phantom lines. The wires 8 are made of or contain a metallic or plastic material. In accordance with a feature of the invention, the tube 1 includes a curved intermediate portion 9 which is adjacent the distal end 1a and enables the distal end to change its orientation in response to rotation of the tube 1 about its longitudinal axis. Thus, by turning the tube 1 in a clockwise or in a counterclockwise direction at the time the distal end 1a is located at the junction of the branch passages 5 and 4, the person in charge can move the distal end 1a to an optimum position for entry into the passage 4 in response to further longitudinal advancement of the tube 1 into the heart.

The intermediate portion 9 of the tube 1 which is shown in FIGS. 1 to 3 exhibits a tendency to assume the curved shape which is best shown in FIG. 3. This can be achieved by appropriate treatment of the corresponding portions of the wires 8, e.g., by soft annealing. The intermediate portion 9 of FIG. 3 has a constant curvature, i.e., it curves gently all the way between its two ends.

The intermediate portion 9' of FIG. 4 is made of a ductile material which is capable of undergoing repeated deformation in a desired direction and to a desired extent, namely as selected by the person in charge prior to introduction of the tube 1 including the intermediate portion 9' into a passage of a human or another animal body. It will be seen that the tube 1 of FIG. 4 is constructed in such a way that the curvature of the intermediate portion 9' is adjustable, not only as concerns the direction in which the adjacent leader 1a (not shown) of the tube extends but also as concerns the extent of inclination of the distal end 1a relative to the adjacent section of the tube 1 behind the intermediate portion 9'. Furthermore, the person in charge can select the exact curvature of the intermediate portion 9' before the tube including the portion 9' is introduced into an animal body to establish a path for introduction of a catheter 2, a cardiac pacemaker electrode or any other elongated medical device.

FIGS. 3 and 4 show that the neighboring convolutions of the wires 8 actually contact each other, even in the region of the intermediate portion 9 or 9'. Only those portions of neighboring convolutions of the wires 8 which are located at the convex sides of the intermediate portions 9 and 9' are slightly spaced apart from one another. The advantage of such design of the tube 1 is that it can properly guide the working end of the catheter toward the obstruction 3 in the branch passage 4.

The tube 1 exhibits a pronounced resistance to turning of the distal end 1a relative to the proximal end 1b or vice versa. This is due to the fact that the tube is made of a plurality of helically wound wires 8 with closely adjacent convolutions. Thus, when the person in charge rotates the tube 1 at the proximal end 1b (e.g., by a rotating means in the form of a handle 10), the distal end 1a shares all angular movements of the proximal end 1b and handle 10. This is highly desirable and advantageous because the intermediate portion 9 or 9' can change the orientation of the distal end 1a in such a way that the distal end confronts the inlet of the branch passage 5 at the junction of the passages 6, 5 and that the distal end 1a confronts the inlet of the branch passage 4 at the junction of the passages 5 and 4. In other words, the person in charge can manipulate the handle 10 (in and counter to the direction which is indicated by arrow Pf1) to turn the tube 1 to a position in which further advancement of the distal end 1a at the junction of the passages 6, 5 does not result in bypassing of the passage 5 and that further advancement of the distal end 1a at the junction of the passages 5, 4 does not result in bypassing of the passage 4.

Pronounced resistance of the tube 1 to turning of its proximal end 1b relative to the distal end 1a exhibits the additional advantage that the catheter 2 can be set in rotary motion, without causing any damage to the tube, at least at a time when its working end approaches the obstruction 3. In many instances, the catheter will be caused to rotate during advancement in the tube 1; this reduces the resistance which the catheter encounters to advancement of its distal end toward and beyond the distal end 1a of the tube.

One presently preferred mode of treating the intermediate portion of the tube 1 made of wires 8 which consist of stainless spring steel is to soft-anneal the wires close to the distal end 1a so that the intermediate portion acquires a desired deformability and tends to retain the deformed shape. The arrangement may be such (FIG. 3) that the intermediate portion 3 is deformed (bent or curved) immediately after soft annealing and then invariably tends to assume the illustrated shape even though it is capable of changing its shape for the purpose of advancing in the passage 6, 5 or 4 and of advancing from the passage 6 into the passage 5 and from the passage 5 into the passage 4. Soft annealing reduces or eliminates the resiliency of the thus treated portions of the wires 8 so that the person in charge can readily select the desired shape of the intermediate portion 9. The portion 9 thereupon tends to reassume such shape as soon as it is capable, i.e., as soon as the magnitude of stresses tending to impart to the portion 9 a different shape than that shown in FIG. 3 is reduced to a value which does not suffice to overcome the innate tendency of the portion 9 to reassume the shape of FIG. 3.

The handle 10 can be replaced with any other suitable means for rotating the distal end 1a of the tube 1 from the proximal end 1b or from any other portion of the tube 1 which is accessible from the exterior of the animal body.

The diameter of a wire 8 is preferably between 0.1 and 0.3 mm. Though the drawing shows a tube 1 wherein the number of wires is eight in each of its sections, it is within the purview of the invention to modify the tube by using a larger number of wires to make a major or longer first section (including the proximal end 1b) and a lesser number of wires to make the other or second section including the distal end 1a and the intermediate portion 9 or 9'. For example, the number (m) of wires in the first section can be between six and ten, and the number (m-n) of wires in the second section can be between two and five.

The larger-diameter hose or sleeve 7 is used to introduce the tube 1 of the improved guide into and passage 6 and to facilitate advancement of the tube 1 toward the junction of the passages 6 and 5. The hose 7 can be made of a plastic material and the tube 1 advances through and beyond this hose by moving in one of the directions which are indicated by a double-headed arrow Pf1. The tube 1 is thereupon rotated in or counter to the direction which is indicated by the arrow Pf2 not later than when the distal end 1a reaches the junction of the passages 5 and 4. The angular movement of the tube 1 (such angular movement is imparted by way of the handle 10 at the proximal end 1b) is terminated when the distal end 1a confronts the inlet of the passage 4 under the action of the intermediate portion 9 which tends to assume the arcuate shape of FIG. 3 and thus enables the distal end 1a to face in a selected direction. Advancement of the distal end 1a in the passage 5 (toward the junction of the passages 5 and 4) can take place simultaneously with rotation of the tube by turning the proximal end 1b with the handle 10. The curvature of the intermediate portion 9 is sufficiently pronounced to ensure that the distal end 1a enters the passage 4 (rather than advancing beyond the junction of the passages 5 and 4) if the person in charge continues to advance the tube deeper into the heart. The catheter 2 can be introduced into, and its working end advanced beyond, the distal end 1a and toward engagement with the obstruction 3 after the distal end 1a assumes the position (in the branch passage 4) which is shown in FIG. 1. The catheter 2 is set in rotary motion not later than when it reaches the obstruction 3.

An advantage of the improved guide is that its tube 1 can resist a pronounced tendency of the proximal end 1b to turn relative to the distal end 1a. This is desirable on two grounds. Thus, the intermediate portion 9 can be caused to select the orientation of the distal end 1a (for the purpose of entering the passage 5 from the passage 6 and of entering the passage 4 from the passage 5) by the simple expedient of turning the handle 10. Secondly, the distal end 1a of the tube 1 can be held (by handle 10) against rotation when the catheter 2 is rotated while it approaches, or at least while it penetrates into, the obstruction 3. The just discussed ability of the tube 1 to prevent rotation of the proximal end 1b relative to the distal end 1a and/or vice versa is achieved while at least the major part of the tube 1 exhibits a highly desirable flexibility so that it can be caused to follow the paths which are defined by the mutually inclined passages 6, 5 and 4 in the heart. Pronounced flexibility of the tube 1 is particularly desirable at the junctions of the passages 6, 5 and 5, 4. It must be borne in mind that these junctions cause successive increments of the tube 1 to flex while the tube is caused to advance toward the obstruction 3. The just described desirable and advantageous (but at a first glance conflicting or mutually exclusive) characteristics of the improved guide are arrived at by the expedient of making the tube 1 from a plurality of helically wound wires 8 rather than from a single helically wound wire. The diameters of the wires 8 are relatively small (preferably between 0.1 and 0.3 mm) in order to ensure that the tube 1 is a thin-walled hollow flexible body. The diameter of the tube 1 should barely suffice to permit advancement of the catheter 2 toward and beyond the distal end 1a with a minimum of resistance. A small-diameter tube 1 is preferred in order to ensure that the inserted tube cannot unduly interfere with the flow of blood in the passages 6, 5 and 4 as well as in the passages which branch off these passages. This is particularly important in connection with the relatively narrow branch passages 5 and 4.

The catheter 2 or another elongated medical device which is to be introduced into an animal body with assistance from the tube 1 should be readily flexible so that it can undergo deformation which is necessary to advance from the passage 6 into the passage 5 and from the passage 5 into the passage 4 on its way toward the obstruction 3 in the heart or in any other part of an animal body which is to be penetrated into by a rotary or other catheter, by a pacemaker electrode or the like.

FIG. 4 shows the distal end of the tubular envelope 11. This envelope can be made of a suitable flexible plastic material and can be shrunk onto the first section of the tube 1 to preferably terminate short of the intermediate portion 9′, i.e., the intermediate portion and the distal end 1a remain unconfined. An advantage of the envelope 11 is that it further reduces the likelihood of turning of the distal end 1a relative to the proximal end 1b and/or vice versa. An advantage of utilizing an envelope 11 which does not surround the tube 1 all the way to the distal end 1a is that the flexibility of the section including the intermediate portion 9′ and the distal end 1a is not affected by the envelope and can be even more pronounced than the flexibility of the other (major) section of the tube. Pronounced flexibility of the section including the intermediate portion 9′ and the distal end 1a is desirable and advantageous because this ensures that rotation of the tube 1 by way of the handle 10 can lead to proper orientation of the distal end 1a for the purpose of entering the inlet of the passage 5 and thereupon the inlet of the passage 4.

The envelope 11 can be used with equal advantage on the tube 1 of FIGS. 1 to 3, i.e., on a tube which has an intermediate portion (9) continuously tending to assume the shape which is shown in FIG. 3.

The main difference between the intermediate portions 9 and 9′ is that the material of the portion 9′ is ductile (or more ductile than the material of the intermediate portion 9) so that a person in charge can deform the corresponding portions of the wires 8 just before the tube including the intermediate portion 9′ is caused to enter a cavity in an animal body. Thus, the person in charge can select the curvature of the intermediate portion 9′ to be optimally suited for introduction into a particular passage or branch passage, i.e., into a passage having a particular shape and being reachable by advancing the leader 1a of the tube 1 through one or more junctions between passages leading to the locus of final destination of the distal end of a catheter 2 or another flexible medical device.

The proximal end 1b of the tube 1 would be free to turn relative to the distal end 1a and vice versa (i.e., the resistance of the tube to torsional stresses would be unsatisfactory) if the tube were made of a single helically wound wire. The inability of the tube to resist torsional stresses (i.e., rotation of the distal and proximal ends relative to each other) would prevent the person in charge from properly orienting the distal end so that the outlet of the distal end would face the inlet of the passage 5 at the junction of the passage 6, 5 and the inlet of the passage 4 at the junction of the passages 5 and 4. As mentioned above, it is preferred to wind two or more wires 8 in such a way that neighboring convolutions of the wound wires actually contact each other. This contributes to smoothness of the internal and external surfaces of the tube 1 and thus facilitates introduction of the tube into the passages 6, 5, 4 and introduction of the catheter into the tube.

It has been found that a high-quality tube which is useful for long periods of time can be obtained from wires which are made of stainless spring steel. Such tube can be sterilized and exhibits a highly satisfactory (pronounced) flexibility. Moreover, the curved intermediate portion 9 can be formed in a very simple and predictable manner by soft annealing the corresponding portions of the wires 8, i.e., by reducing or eliminating the resiliency of selected portions of the wires so that the intermediate portion (9) invariably tends to assume the imparted shape or that the intermediate portion (9') is sufficiently ductile to permit selection of its curvature immediately prior to introduction of the tube 1 into an animal body. Such introduction is monitored on a screen in a conventional manner, i.e., the person in charge can observe the orientation of the distal end 1a and is in a position to turn the tube 1 via handle 10 until the distal end 1a faces the inlet of the passage 5 and thereupon the inlet of the passage 4.

A satisfactory compromise between desirable pronounced flexibility and desirable resistance to torsional stresses can be reached if the tube 1 consists of at least two (preferably at least three or four) and not more than ten (preferably between five and ten and most preferably seven or eight) wires. Experiments indicate that the tube 1 exhibits a highly satisfactory flexibility as well as a highly satisfactory resistance of the ends 1a, 1b to turn relative to each other if the tube is made of eight helically wound wires 8. This ensures that each of the eight wires 8 has a rather pronounced lead in spite of the fact that the neighboring convolutions of the wires actually contact each other. The neighboring convolutions of eight discrete wires 8 support and stabilize each other even if the diameters of the wires do not or need not exceed 0.3 mm, i.e., even though the wall thickness of the tube 1 is minimal. A wall thickness of 0.2 mm has been found to be very satisfactory.

As mentioned above, the number of wires in that section of the tube 1 which includes the distal end 1a and the intermediate portion 9 or 9' can be less than the number of wires in the other section which extends from the intermediate portion 9 or 9' to the proximal end 1b. This enhances the flexibility of the section including the distal end 1a and the intermediate portion 9 or 9'. In addition, it has been found that reaction forces (which necessitate pronounced resistance to torsional stresses) are smaller in the region of the distal end 1 and of the adjacent intermediate portion 9 or 9'. The major section of the tube can consist of between six and ten wires 8, and the remaining section (including the distal end 1a and the intermediate portion 9 or 9') can consist of between two and five (preferably three or four) wires 8.

In lieu of making the envelope 11 from prefabricated tubular stock which is shrunk onto the major portion of the tube 1, the envelope can be made by spraying or otherwise applying plasticized material directly onto the external surface of a selected length of the tube 1. The external surface of the envelope 11 is preferably smooth to thus ensure that it offers a minimum of resistance to introduction of the tube 1 into the passages 6, 5 and 4. At the same time, even a very thin and highly flexible envelope 11 enhances the resistance of the tube 1 to torsional stresses. Though the envelope 11 can extend all the way to and can also confine the distal end 1a, it is presently preferred to select the length of the envelope in such a way that the distal end 1a and the intermediate portion 9 or 9' of the tube remain exposed. This ensures that the section including the distal end 1a and the intermediate portion 9 or 9' can exhibit a very pronounced flexibility.

As said before, the envelope can also cover the tube totally. It may even exceed the distal end in order to make the edge as smooth as possible. The envelope covering the intermediate part can also help to shape the desired curve of the guiding tube.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A guide for introduction of catheters, pacemaker electrodes and analogous elongated medical devices into branch passageways of animal bodies which can be entered by changing the direction of advancement of the medical devices, comprising a plurality of closely adjacent helically wound wires together forming a single elongated flexible rotary tube having a distal end, a proximal end and an intermediate portion adjacent said distal end, said intermediate portion being rotatable in response to rotation of said proximal end and said distal end being rotatable in response to rotation of said intermediate portion, said intermediate portion having the tendency to assume a curved shape so as to change the orientation of said distal end in response to rotation of said proximal end.

2. The guide of claim 1, wherein said wires include metallic wires.

3. The guide of claim 1, wherein said wires include plastic wires.

4. The guide of claim 1, wherein said wires have neighboring convolutions which are in contact with each other.

5. The guide of claim 1, wherein said wires consist of spring steel and include soft annealed sections which together form said intermediate portion of said tube.

6. The guide of claim 1, wherein said wires consist of spring steel and include ductile sections which together form said intermediate portion of said tube.

7. The guide of claim 1, wherein said proximal end includes means for rotating said intermediate portion.

8. The guide of claim 7, wherein said means for rotating comprises a handle.

9. The guide of claim 1, wherein said tube consists of between two and ten helically wound wires.

10. The guide of claim 1, wherein said wires consist of corrosion-resistant steel.

11. The guide of claim 1, wherein each of said wires has a diameter of 0.1 to 0.3 mm.

12. The guide of claim 1, wherein said tube includes a first section adjacent said proximal end and a second section adjacent said distal end and including said intermediate portion, said first section consisting of m helically wound wires and said second section consisting of m-n helically wound wires, m and n being whole numbers and m being greater than n.

13. The guide of claim 12, wherein said first section consists of between six and ten helically wound wires and said second section consists of between two and five helically wound wires.

14. The guide of claim 1, further comprising a flexible tubular envelope surrounding at least a portion of said tube.

15. The guide of claim 14, wherein said envelope contains a plastic material.

16. The guide of claim 14, wherein said envelope is shrunk onto said tube.

17. The guide of claim 14, wherein said distal end extends beyond said envelope.

18. The guide of claim 14, wherein said distal end and said intermediate portion extend beyond said envelope.

* * * * *